United States Patent [19]

Meduri

[11] Patent Number: 5,297,560
[45] Date of Patent: Mar. 29, 1994

[54] METHOD OF PROTECTED BRONCHIAL SAMPLING USING A TRANSLARYNGOSCOPIC CATHETER

[75] Inventor: G. Umberto Meduri, Memphis, Tenn.

[73] Assignee: Mill-Rose Laboratories, Inc., Mentor, Ohio

[21] Appl. No.: 866,734

[22] Filed: Apr. 10, 1992

[51] Int. Cl.⁵ .............................................. A61B 10/00
[52] U.S. Cl. ............................................... 128/756
[58] Field of Search ................... 128/10, 11, 756, 749

[56] References Cited

U.S. PATENT DOCUMENTS

| | | | |
|---|---|---|---|
| 3,830,225 | 8/1974 | Shinnick | 128/756 |
| 4,946,440 | 8/1990 | Hall | 128/756 |
| 4,966,162 | 10/1990 | Wang | 128/756 |
| 5,056,529 | 10/1991 | de Groot | 128/756 |

OTHER PUBLICATIONS

Meditech Contamination Free Microbiology Specimen Brush, Meditech, Feb. 1979.
Principles and Practices of Infections Diseases, (3d.ed), 1990, authored by G. Mandell, published by Churchill Livingstone, p. 546.

*Primary Examiner*—Max Hindenburg
*Attorney, Agent, or Firm*—Watts, Hoffmann, Fisher & Heinke Co.

[57] ABSTRACT

A method of collection of uncontaminated secretions from the lower respiratory tract of non-intubated patients using a laryngoscope and a translaryngoscopic catheter. After properly positioning the insertion tube of a laryngoscope in the larynx of a patient, the translaryngoscopic catheter is inserted through the instrument channel of the laryngoscope and a sampling element disposed within the lumen of the catheter is exposed to secretions in the lower respiratory tract. The sampling element is retracted and removed from the catheter. Fluid is injected into the tracheobronchial tree through the catheter and aspirated back.

12 Claims, 4 Drawing Sheets

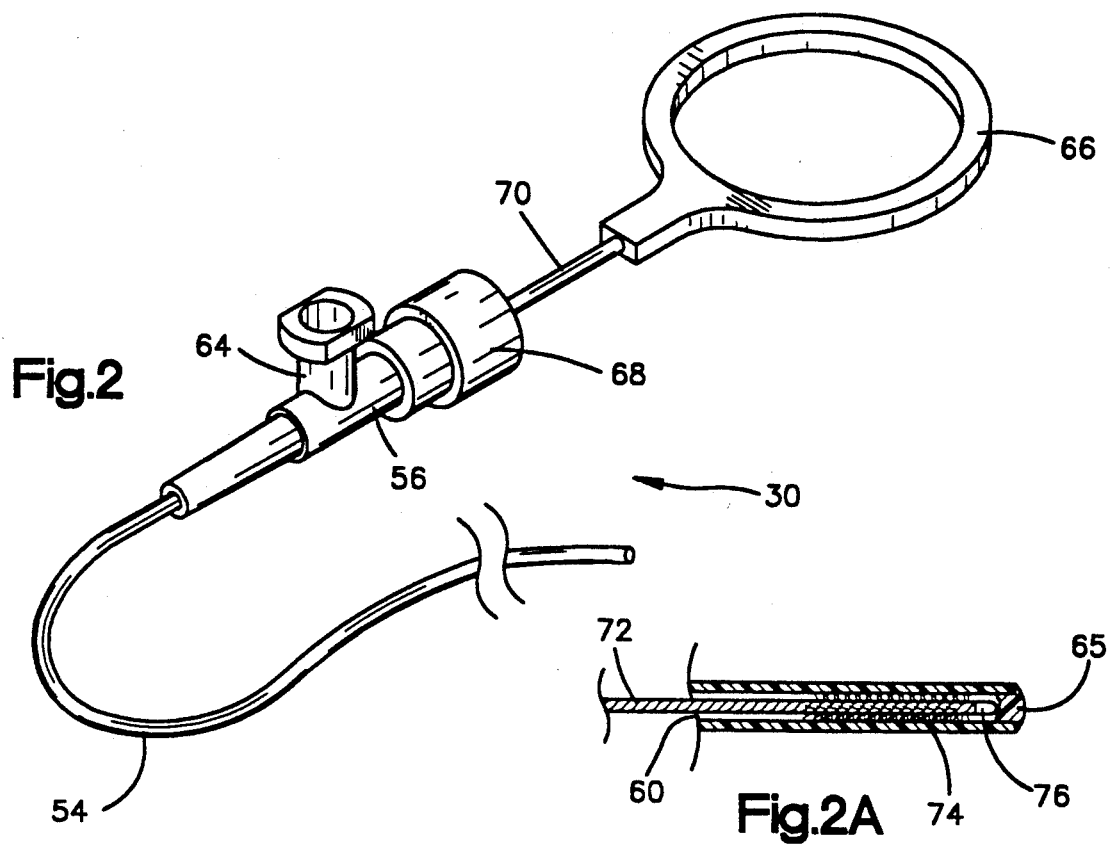
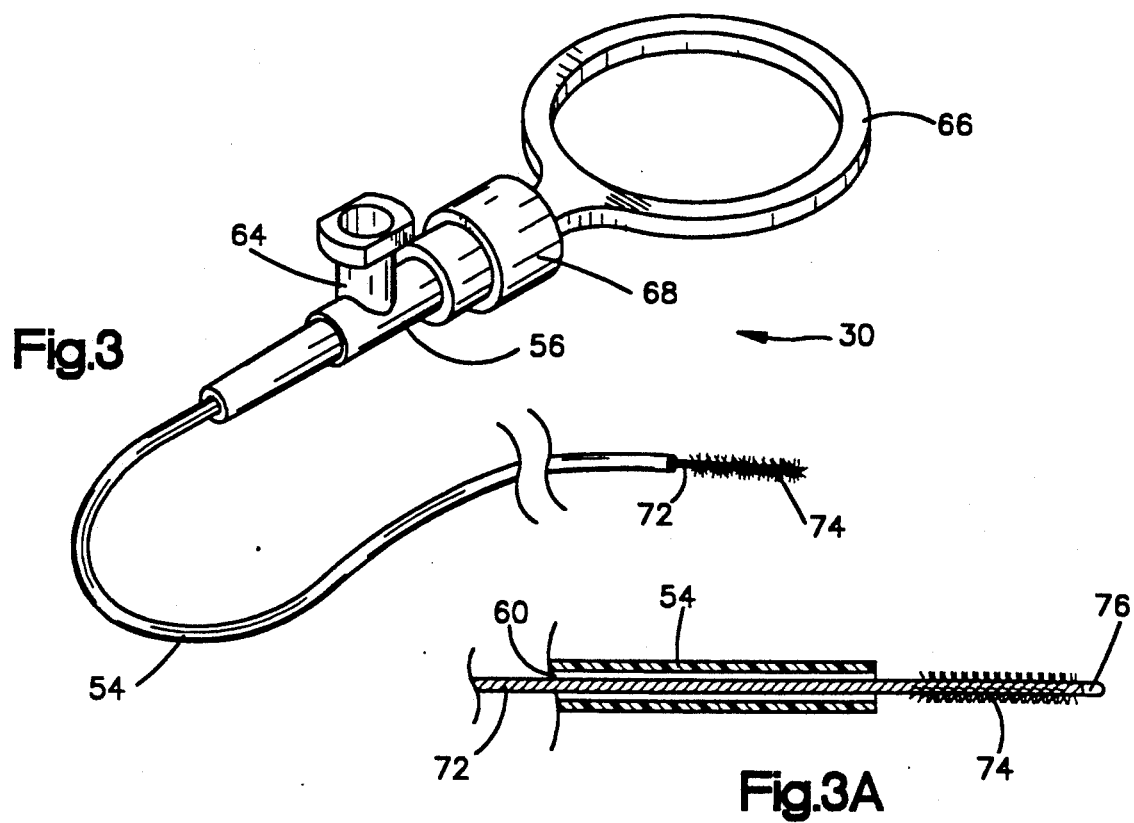

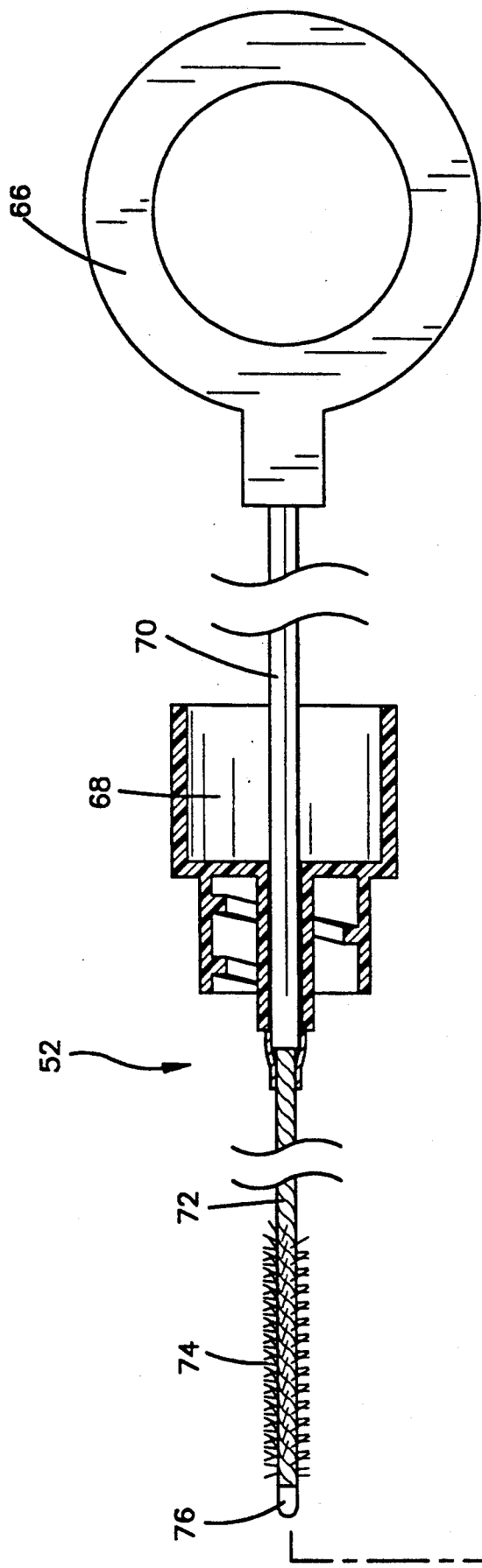
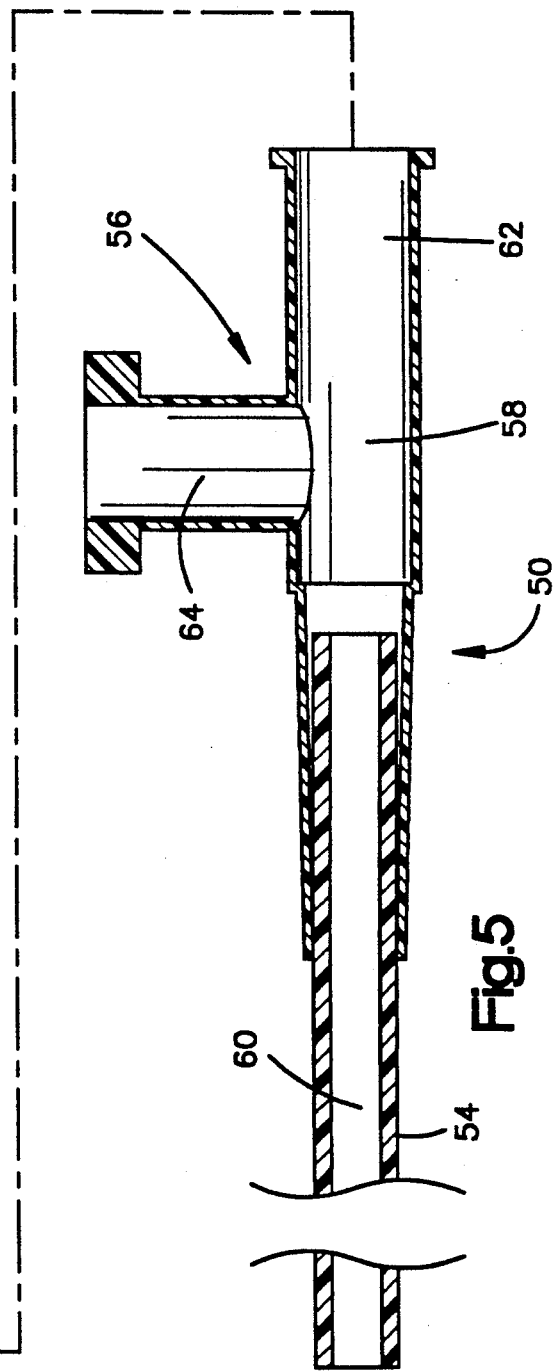
Fig.5

METHOD OF PROTECTED BRONCHIAL SAMPLING USING A TRANSLARYNGOSCOPIC CATHETER

BACKGROUND OF THE INVENTION

The present invention relates to a method of diagnosing lung infections of a patient and more particularly, a method of collecting uncontaminated secretions from the lower respiratory tract of a patient using a laryngoscope and a translaryngoscopic catheter.

DESCRIPTION OF RELATED ART

Pneumonia is a common infection that carries, in a certain group of patients, a high mortality rate. The treatment of bacterial infections of the lower respiratory tract is remarkably simplified when the responsible pathogen is accurately defined, allowing institution of the most effective and narrow spectrum antibiotic therapy. To establish an etiologic diagnosis of pneumonia, the physicians traditionally rely on the findings of microscopic and culture analysis of the sputum. This time-honored practice, however, has proven limitations. Quality sputum samples can be obtained in only 50% of patients with community-acquired pneumonia. The oropharynx is normally colonized by complex microbial flora containing organisms at a high concentration, easily contaminating secretions expectorated from the lower respiratory tract. Contamination is particularly troublesome in seriously ill patients who frequently have the upper airways colonized with potential pathogens, making it difficult or impossible to differentiate infecting from colonizing bacteria.

Three diagnostic methods have been developed that bypass the oropharynx in order to collect uncontaminated secretions from the lower respiratory tract: (1) bronchoscopy with protected specimen brushing and bronchoalveolar lavage; (2) transtracheal aspiration; and (3) transthoracic needle aspiration. Bronchoscopy with protected specimen brushing and bronchoalveolar lavage allows for the identification of the presence or absence of pneumonia with a high degree of certainty; however, this technique has the drawback of being an invasive procedure that can be performed by a limited group of specialized physicians who are experienced in bronchoscopy.

Transtracheal aspiration and transthoracic needle aspiration have been extensively investigated but both of these highly invasive procedures have fallen into disfavor because of the risk of serious complications (bleeding and subcutaneous emphysema) and the evolution in recent years of newer bronchoscopic techniques.

SUMMARY OF THE INVENTION

A purpose of this invention is to provide a method of diagnosing pneumonia with a high degree of certainty by collecting uncontaminated secretions from the lower respiratory tract, but that is less invasive than present methods of bronchoscopy with protected specimen brushing, transtracheal aspiration and transthoracic needle aspiration, and that can be practiced by a greater number of physicians who do not have specialized training in bronchoscopy.

Broadly, the method comprises passing the insertion tube of a flexible fiberoptic laryngoscope into the larynx of a patient, inserting a translaryngoscopic catheter having a sampling element within the lumen of the catheter through the instrument channel of the laryngoscope and into the trachea of the patient, advancing the sampling element from the catheter into the trachea or a mainstem bronchus, retracting the sampling element into the catheter, and removing the sampling element from the catheter for analysis of the uncontaminated secretions on the sampling element. Additionally, the method will often include injecting a fluid through the catheter into the tracheobronchial tree of the patient and aspirating the fluid back through the catheter.

BRIEF DESCRIPTION OF THE DRAWINGS

Preferred embodiments of the invention are shown in the accompanying drawings in which:

FIG. 2 is a perspective view of the translaryngoscopic catheter of FIG. 1 with the sampling element in the retracted position;

FIG. 2A is an enlarged fragmentary view of the distal portion of the translaryngoscopic catheter of FIG. 1 with the sampling element in the retracted position;

FIG. 3 is a perspective view of the translaryngoscopic catheter with the sampling element in the advanced position;

FIG. 3A is an enlarged fragmentary view of the distal portion of the translaryngoscopic catheter of FIG. 1 with the sampling element in the advanced position;

FIG. 5 is a sectional view of the translaryngoscopic catheter of FIG. 1 in disassembled condition.

BEST MODE FOR PRACTICING THE INVENTION

Figure 1:
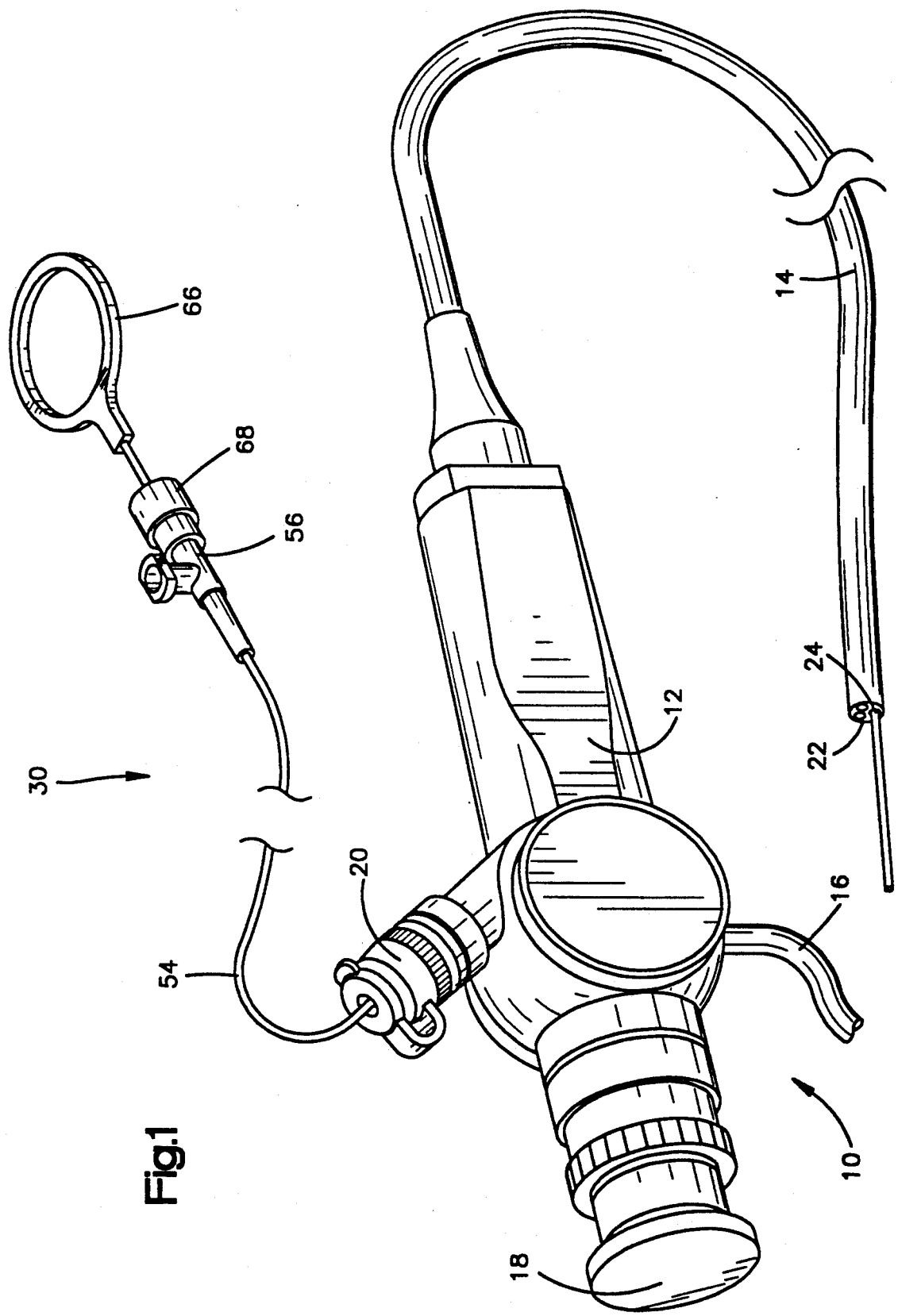
FIG. 1 is a perspective view of a laryngoscope with a translaryngoscopic catheter advanced through the instrument channel of the laryngoscope.

In the practice of the method of this invention to collect uncontaminated secretions from the lower respiratory tract of a patient, a laryngoscope 10 and translaryngoscopic catheter 30, as shown generally in FIG. 1, are used. The laryngoscope 10 is of conventional design and comprises a body portion 12, an insertion tube 14, a power source connector 16, an eyepiece 18, and a side entry port 20. The laryngoscope insertion tube 14 is of sufficient length to allow for the examination of the nasopharynx of a patient down to the vocal chords and trachea, and has an optical system with an objective lens and light guides 22 at its distal end which allows a physician to visualize the nasopharynx, vocal chords and trachea of a patient through the eyepiece 18 as the insertion tube 14 is routed through the nasal system of the patient. The laryngoscope 10 has an instrument channel 22 within the insertion tube 14 which is accessible through the side entry port 20.

The translaryngoscopic catheter 30 comprises an outer member 50 and a second member 52 which can be disassembled from the outer member, as shown in FIG. 5. The outer member 50 comprises flexible tubing 54 which is secured to a fitting 56. The preferred and illustrated fitting 56 is a "T" luer adaptor fitting. The fitting 56 includes a central cavity 58 communicating with the lumen 60 of the flexible tubing 54. Two female luer connectors 62, 64 are formed on the fitting 56 to communicate with the central cavity 58. The first connector 62 is in axial alignment with the cavity 58 and the second 64 is normal thereto. A biodegradable plug 65, such as shown in U.S. Pat. No. 4,235,244, is disposed within the distal end of the flexible tubing 54.

The second member 52 of the translaryngoscopic catheter comprises an actuator 66, a fitting cap 68, a rod 70, a pair of flexible twisted wires 72, a sampling element 74 which in the preferred embodiment is a brush, and an endcap 76. At the distal end of the inner member 52, the sampling element 74 is clamped between a portion of the twisted wires 72 adjacent the endcap 76, which is secured to the tip of the sampling element 74. The endcap 76 serves to blunt the tip of the sampling element. At the proximal end of the second member 52, a rod 70 is attached to the proximal end of the pair of twisted wires 72. An actuator 66 is attached to the proximal end of the rod 70. A fitting cap 68 having a male luer fitting 78 and a bore 80 is slidably disposed on the rod 70, its movement being limited by the distal end of the actuator 66 and the point of attachment between the pair of twisted wires 72 and the rod 70.

Figure 4:
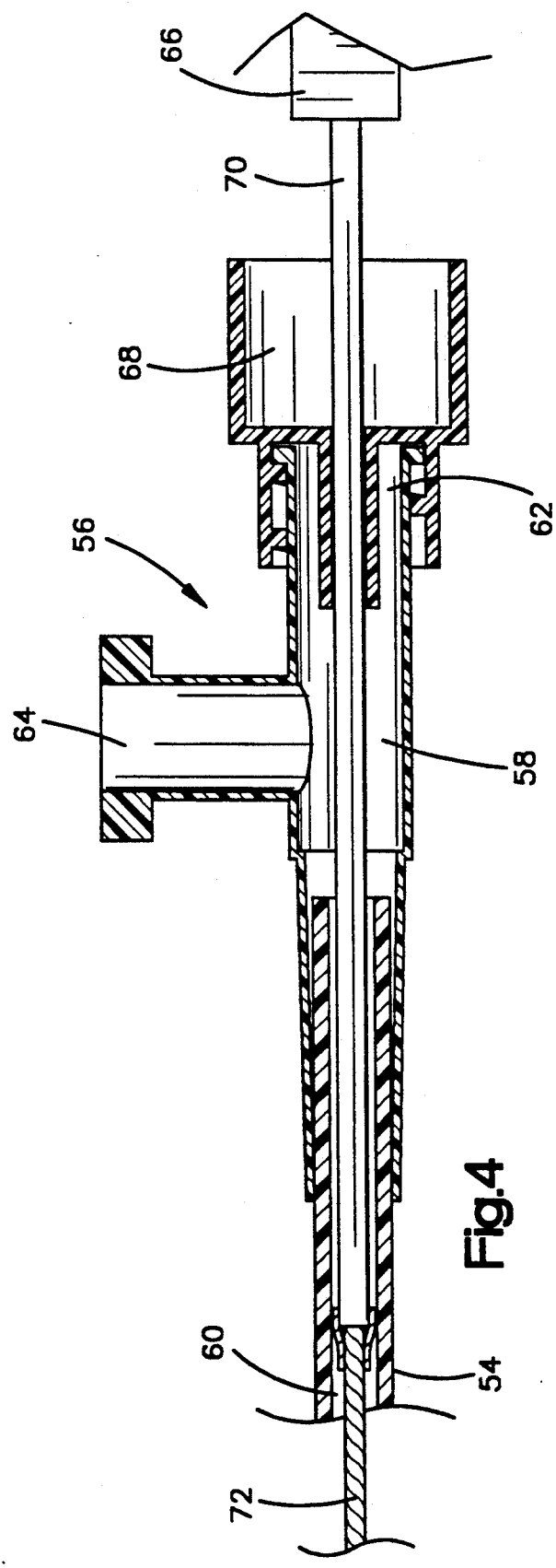
FIG. 4 is an enlarged sectional view of a portion of the proximal end of the translaryngoscopic catheter of FIG. 1 in assembled condition.

When the translaryngoscopic catheter 30 is in its assembled condition as shown in FIGS. 2, 3 and 4, the pair of twisted wires and sampling element 74 of the second member 52 are disposed within the outer member 58. The cap 68 of the second member being threaded onto the female luer connector 62 of the fitting 56 of the outer member 50, as shown in FIG. 4. When the sampling element 74 is in the retracted position, as shown in FIG. 2, the sampling element is disposed in the lumen 60 of the flexible tube 54 near the proximal end of the biodegradable plug 65. When the sampling element 74 is in the advanced position, as shown in FIG. 3, the sampling element is extended beyond the distal end of the flexible tube 54, the biodegradable plug 65 having been ejected from the lumen 60 of the tube.

After appropriate sedation of the patient and local anesthesia of the nose, the insertion tube 14 of a laryngoscope 10 is inserted into the nasal passage of a patient and is passed into the larynx of the patient to visualize the vocal cords. The translaryngoscope catheter 30 is advanced through the instrument channel 22 of the laryngoscope 10 past the vocal cords to a point where the distal end of the catheter is positioned in the lower portion of the trachea next to the carina of the patient.

The actuator 66 is depressed, ejecting the biodegradable plug 65 from the lumen 60 and advancing the sampling element 74 into the trachea or mainstem bronchus of the patient. The actuator 66 is manipulated to introduce the sampling element into secretions in the lower respiratory tract visible through the laryngoscope optical system. When the sampling is completed, the actuator 66 is returned to its initial position and the sampling element 74 is retracted into the lumen 60 of the tube 54. The fitting cap 68 is disconnected from the fitting 56 and the inner member 52 of the catheter is removed from the outer member 50. The sampling element 74 is then severed from the pair of twisted wires 72 and placed in a vial of thioglycollate broth.

A 30 ml. syringe with sterile non-bacteriatic saline is attached to the main port connector 62 of the fitting 56. The saline solution is injected through the translyrngoscopic catheter into the tracheobronchial tree of the patient. The saline solution in the tracheobronchial tree is then aspirated back into the syringe.

The sampling element 74 and the aspirate are subsequently processed and subjected to microscopic and microbiologic analysis to diagnose the patient's lung infection.

Thus, without the use of invasive techniques or equipment used only by specialized physicians, as previously required, the method of this invention provides uncontaminated samplings from the lower respiratory tract.

While the best mode for practicing the present invention has been described in detail, it will be apparent that various modifications or alterations may be made therein without departing from the spirit and scope of the invention, set forth in the appended claims.

I claim:

1. In a method of diagnosing disease of a patient, the disease being associated with the lungs, by protected sampling of tracheal or mainstem bronchial secretions using a laryngoscope and a catheter adapted to pass through an instrument channel of a laryngoscope insertion tube, the catheter including a lumen, a sampling element slideably disposed in the lumen and an actuating means for advancing, retracting and manipulating the sampling element, the steps comprising:
   a. passing the insertion tube of a laryngoscope through the nasal passage of the patient and positioning a distal end of the insertion tube in the larynx of the patient;
   b. advancing the translaryngoscopic catheter through the instrument channel of the laryngoscope and into the trachea of the patient;
   c. positioning the distal end of the translaryngoscopic catheter into the lower portion of the trachea of the patient;
   d. advancing the sampling element from the lumen of the translaryngoscopic catheter into either the trachea or a mainstem bronchus;
   e. manipulating the sampling element to contact and sample the secretions present in the trachea or a mainstem bronchus;
   f. retracting the sampling element into the lumen of the translaryngoscopic catheter;
   g. retracting the sampling element through the lumen of the translaryngoscopic catheter and removing the element from the translaryngoscopic catheter;
   h. removing the translaryngoscopic catheter from the instrument channel of the laryngoscope; and
   i. removing the insertion tube of the laryngoscope from the larynx of the patient.

2. In a method as set forth in claim 1, the step of visualizing the vocal cords and airways below the vocal cords through the laryngoscope before advancing the translaryngoscopic catheter into the trachea.

3. In the method as set forth in claim 1 or 2, after the sampling element has been removed from translaryngoscopic catheter, the step of injecting a fluid through the lumen of the translaryngoscopic catheter into a tracheobronchial tree of the patient, and aspirating the fluid back from the tracheobronchial tree of the patient through the lumen of the translaryngoscopic catheter.

4. In the method as set forth in claim 1 or 2, wherein the sampling device is at a distal end of a wire that extends through the translaryngoscopic catheter, the step of removing the sampling device from the wire.

5. In the method as set forth in claim 1 or 2, wherein the sampling element is sealed within the lumen of the translaryngoscopic catheter by a biodegradable plug while the distal end of the catheter is positioned into the lower portion of the trachea, including the step of ejecting the plug from the catheter as the sampling element is advanced from the catheter.

6. A method of obtaining uncontaminated secretions from the trachea or mainstem bronchus of a non-intubated patient comprising the steps of:
   a. positioning the distal end of an insertion tube of a laryngoscope into the larynx of a patient;
   b. visualizing the vocal cords and airways below the vocal cords through the laryngoscope;
   c. advancing a translaryngoscopic catheter through the instrument channel of the laryngoscope and into the trachea of the patient;
   d. positioning the tip of the translaryngoscopic catheter into the lower portion of the trachea of the patient;
   e. advancing a sampling element from the lumen of the translaryngoscopic catheter into either the trachea or a mainstem bronchus;
   f. manipulating the sampling element so as to contact and obtain a sample of the secretions present in the trachea or a mainstem bronchus; and
   g. retracting the sampling element into the lumen of the translaryngoscopic catheter.

7. A method as set forth in claim 6, after the step of retracting the sampling element into the lumen of the translaryngoscopic catheter, the step of removing the sampling element from the lumen of the translaryngoscopic catheter.

8. A method as set forth in claim 7, after the step of removing the sampling element from the translaryngoscopic catheter, the step of injecting a fluid through the lumen of the translaryngoscopic catheter into a tracheobronchial tree of the patient through the lumen of the translaryngoscopic catheter.

9. A method as set forth in claim 8 or 7, wherein the sampling device is at a distal end of a wire that extends through the translaryngoscopic catheter, the step of removing the sampling device from the wire.

10. A method as set forth in claim 8 or 7, wherein the sampling element is sealed within the lumen of the translaryngoscopic catheter by a biodegradable plug while the distal end of the catheter is positioned into the lower portion of the trachea, including the step of ejecting the plug from the catheter as the sampling element is advanced from the lumen of the catheter.

11. Apparatus for use in diagnosing disease associated with the lungs of a patient by obtaining an uncontaminated sample of tracheal or mainstem bronchial secretions and obtaining aspirate from the tracheobronchial tree of a patient, said apparatus comprising:
   a. a laryngoscope having an optical system and instrument channel, and
   b. a translaryngoscope secretion collection and aspiration device insertable into the instrument channel of the laryngoscope and comprising a catheter, said catheter being substantially greater in length than the instrument channel, having a distal end extendable from a distal end of the instrument channel, and having a lumen, a wire within and movable along the lumen, a sampling device attached to the distal end of the wire and located within and spaced from the distal end of the catheter, a biodegradable plug sealing the distal end of the lumen, a fitting attached to the proximal end of the catheter and including a central cavity in communication with the lumen, the fitting further having a side port adapted for the injection of fluid into and aspiration of fluid from a tracheobronchial tree of the patient, an actuator means proximal to the fitting and attached to the wire for advancing, retracting and manipulating said sampling element and a fitting cap intermediate the fitting and the actuation means and removably attached to a proximal end of said fitting, the cap cooperating with the actuator means to limit the advancement and retraction of the sampling element and allowing, upon removal of the cap from the fitting, the withdrawal of the sampling element from the lumen of the translaryngoscopic catheter.

12. The apparatus of claim 11, wherein the sampling element is a brush.

* * * * *